United States Patent
Fletcher

(10) Patent No.: US 7,051,593 B2
(45) Date of Patent: May 30, 2006

(54) VIBRATION TESTING APPARATUS AND A METHOD OF VIBRATION TESTING

(75) Inventor: Mathew David Fletcher, Royston Hertfordshire (GB)

(73) Assignee: Ling Dynamic Systems, Inc., Yalesville, CT (US)

( * ) Notice: Subject to any disclaimer, the term of this patent is extended or adjusted under 35 U.S.C. 154(b) by 0 days.

(21) Appl. No.: 10/849,898

(22) Filed: May 21, 2004

(65) Prior Publication Data

US 2005/0257619 A1 Nov. 24, 2005

(51) Int. Cl.
*G01M 7/06* (2006.01)

(52) U.S. Cl. .............................. 73/665; 73/667; 73/668

(58) Field of Classification Search ................ 73/662, 73/663, 665, 666, 668
See application file for complete search history.

(56) References Cited

U.S. PATENT DOCUMENTS

| | | | | |
|---|---|---|---|---|
| 3,020,751 A | * | 2/1962 | Wohl | 73/668 |
| 3,583,205 A | * | 6/1971 | Erle | 73/1.87 |
| 4,489,612 A | | 12/1984 | Griggs | 73/663 |
| 4,715,229 A | * | 12/1987 | Butts | 73/663 |
| 5,351,545 A | * | 10/1994 | Lucas | 73/663 |
| 6,131,461 A | * | 10/2000 | Leist | 73/662 |
| 6,443,013 B1 | * | 9/2002 | Smith et al. | 73/663 |
| 6,543,289 B1 | * | 4/2003 | Jinzenji et al. | 73/668 |

FOREIGN PATENT DOCUMENTS

| | | | |
|---|---|---|---|
| GB | 2156166 | | 1/1985 |
| GB | 2183002 A | * | 5/1987 |
| GB | 2211268 | | 10/1987 |
| GB | 2217521 | | 4/1988 |
| GB | 2236434 | | 9/1989 |
| JP | 200146748 A | * | 5/2000 |

\* cited by examiner

*Primary Examiner*—Hezron Williams
*Assistant Examiner*—Rose M. Miller
(74) *Attorney, Agent, or Firm*—Baker & Hostetler

(57) ABSTRACT

In order to provide a vibration testing apparatus which can have a large diameter without introducing undesirable rigid vibration modes, the vibration testing apparatus 1 comprises a support 2, at least one electromagnetic vibration generator 12 mounted on the support, the mounting comprising an annular body 5 and a head expander 10, the annular body being supported by bearings located around the periphery of the annular body 5.

25 Claims, 4 Drawing Sheets

VIBRATION TESTING APPARATUS AND A METHOD OF VIBRATION TESTING

FIELD OF THE INVENTION

The present invention relates to a vibration testing apparatus, in particular a large diameter vibration testing apparatus and a method of vibration testing using this apparatus.

BACKGROUND OF THE INVENTION

A vibration testing apparatus, sometimes known as a shaker, is employed in industry for the vibration testing of industrial elements and components. The object of such vibration testing apparatus is to expose scientific or industrial equipment to vibration of the frequency and amplitude to which that equipment may be exposed in normal use, to test the response of the equipment to the vibrations.

The present invention is particularly concerned with the vibration testing of satellites. These satellites are typically exposed to very severe vibrations during launch. These vibrations may have frequencies in the range 5–150 Hz.

A vibration testing apparatus is shown in U.S. Pat. No. 4,489,612. This includes an electromagnetic vibration generator which is mounted on a trunion which is arranged, in one configuration, to vibrate a slip plate in a horizontal plane. The slip plate is mounted on a massive support block through hydrostatic bearings. Hydrostatic bearings are employed because they give the lowest distortion and the highest stiffness to the bearing.

The electromagnetic vibration generator can also be mounted in a configuration in which the armature is oriented vertically and can supply vibration to an object mounted directly on the armature. Where the object is of a larger size than the armature, a so-called head expander maybe used, for example as disclosed in GB2211268.

In order to test the vibration modes of the equipment being tested in the frequency range desired, it is preferred to minimise vibration modes of the combination of the vibration testing apparatus and the equipment in this range.

It is normal to design the weight, dimensions and stiffness of various parts of the vibration testing apparatus so that this object is attained.

Vibration modes due to the vibration testing apparatus itself may include flexible vibration modes, for example due to the twisting of the plate. Normally, these vibration modes are of relatively high frequency, falling outside the testing frequency range. However, rigid vibration modes of the head expander, caused by rocking of the head expander within the support structure may be encountered. These may have a frequency which is lower than the flexible modes and may fall within the testing range.

This may be a problem particularly when the equipment being tested has very large dimensions, in particular extending for a large distance away from the expander or when the equipment being tested has a large mass.

Whereas it is known that placing the bearings further apart helps to increase the frequency of rigid vibration modes, this may not be possible because larger dimension mountings have increased mass and hence decreased rigid vibration modes or may be inadequately stiff and have decreased flexible vibration modes.

It is an object of the present invention to provide vibration-testing apparatus in which the amplitude and/or frequency or vibration modes of the combination of the equipment being tested and the vibration testing apparatus can be improved.

SUMMARY OF THE INVENTION

The present invention provides vibration testing apparatus comprising a support, at least one electromagnetic vibration generator mounted on the support, a mounting for mounting equipment to be tested, the mounting being drivable by the electromagnetic vibration generator, wherein the mounting comprises an annular body supported by at least one bearing on the support.

The present invention further provides a method of vibration testing comprising mounting equipment to be tested on a mounting, the mounting being drivable in vibrational modes by at least one electromagnetic vibration generator, the electromagnetic vibration generator being mounted on a support, the mounting comprising an annular body supported by at least one bearing on the support.

The present inventor has realised that many types of equipment to be tested, in particular satellites, are constructed using a ring. That is, the interface between the equipment to be tested and the mounting is annular.

Accordingly, the present inventor has realised that there is no requirement for a mounting structure within the interior of the annulus. There is no requirement for complete area support of the equipment being tested. This in turn allows the mounting to be constructed relatively lightly but with adequate stiffness.

PREFERRED FEATURES OF THE INVENTION

The present invention comprises a support. The support is preferably of a very large mass, or fixable to a structure of very large mass, to provide a stable support for the equipment being tested. For example, the support may have a mass which is at least three times the mass of the equipment of being tested and preferably at least five times the mass of the equipment being tested.

The support preferably does not have any substantial vibration modes in the frequency range being tested.

According to the present invention there is preferably at least one electromagnetic vibration generator. Vibration generators for generating vibrations in the frequency range required are commonly available and are described for example in British patent application No. 2385470 or British patent application no. 2217521.

The electromagnetic vibration generator is mounted on the support in a manner which is known in the art. There may be one, two, three or four vibration generators or, in some cases, more.

According to the invention, the mounting comprises an annular body supported by bearings. By 'annular' it is meant that any parts within the annulus preferably comprise less than 10% of the total weight of the body. Preferably, the mounting consists essentially of an annular body, with substantially no parts within the annulus. In this way, the weight and the strength of the body may be concentrated in the annular region. Accordingly, a mounting which is capable of supporting an annular apparatus to be tested can be provided which has a relatively low mass and a relatively high diameter, so that static vibration modes have a relatively high frequency.

Preferably, the outer diameter of the annular body is at least one meter, preferably at least two meters.

Preferably, the annular body is relatively narrow in the radial direction, having a radial extent of less than 0.5 meters, preferably less than 0.2 meters and most preferably less than 0.1 meters.

The radial extent of the annular body should be selected in order to minimise the generation of vibrations having a frequency within the testing range which are due to flexible buckling modes of the annular body.

The mounting is preferably relatively long in its axial direction, having a depth which is greater than or equal to 0.5 times its diameter, preferably greater than or equal to 0.75 times its diameter. This allows the structure to be relatively stiff.

It is particularly advantageous to have an annular body which is less than 0.1 meters in radial extent but greater than equal 0.7 times its diameter in height.

The annular body is preferably made of a material with a suitable combination of lightness and strength, for example, magnesium alloy, aluminium alloy or any other suitable material.

The annular body need not be solid. It may comprise at least one annular wall provided with radially extending strengthening ribs or webs. There may be at least two circumferentially extending walls joined by radially extending ribs.

Suitably, the mounting comprises an annular body connected at one end to an annular head expander. The head expander is provided to increase the contact width at the end of the annular body. For example, the radial extent of the annular head expander may be up to 0.5 meters and preferably up to 0.2 meters. It may be at least three or at least four times the radial extent of the annular body.

The head expander preferably is comprised of material having a relatively low mass but high strength, for example magnesium or aluminium alloy.

At least one bearing is provided for mounting the annular body in the support. Preferably, there are a plurality of bearings. The bearings are preferably located around the periphery of the annular body. Typically, they are mounted at the top and bottom of the annular body considered in the axial direction. Bearings may be mounted on the inner or outer periphery of the annular body. In a particularly preferred embodiment, bearings are mounted on both inner and outer peripheries of the annular body.

The bearing preferably comprises a hydrostatic bearing. This can give very low distortion and high stiffness. This serves to increase the rigid body modes of the annular body.

In a vibration testing apparatus, it is, as noted above, highly desirable to make the mounting as stiff as possible in at least one direction, in order to resist formation of relatively low frequency rigid modes. According to the present invention, the bearing provides flexibility at least one direction, for transmission of vibrations. The bearing is preferably configured to provide flexibility in the radial direction, being substantially unconstrained in the axial direction and stiff in the tangential direction. By providing flexibility in the radial direction, problems due to thermal expansion can be overcome. Preferably, the bearing does not constrain the mounting in the axial direction. That is, any vibration modes in the axial direction preferably have a frequency which is below the frequency range of interest. In practice, the weight of the equipment being tested and the mounting will be supported by the vibration generator or generators. In this way, the mounting is effectively completely free in the drive direction, so that vibration frequency of the mounting is entirely determined by the operating frequency of the vibration generator.

In a preferred embodiment, the bearing comprise a bearing arm, mounted at one end to the support or to the annular body and at the other end to a bearing, the bearing arm being resiliently flexible in a radial direction but being stiff in the tangential direction. For example, the bearing arm may extend in a substantially tangential direction.

Preferably, the bearing comprises a bearing shaft rotatably mounted in a bearing receiver, the shaft being axially displaceable within the bearing receiver. The shaft may be connected to one of the mounting or the support and the bearing receiver connected to the other of the mounting or support. In this way, the bearing assembly is unconstrained in the axial direction of the shaft. If the axial direction of the shaft is aligned with the axial direction of the annular body, the annular body is unconstrained in the axial direction.

According to the method of the invention, equipment to be tested is mounted on to the mounting, for example by fixing to the head expander. The equipment to be tested may be rigidly fixed to the mounting, to ensure good transfer of vibrational forces.

The electromagnetic vibration generators can then be used to generate vibrational forces which are transferred through the mounting to the equipment to be tested.

There has thus been outlined, in broad terms, the more important features of the invention in order that the detailed description thereof that follows may be better understood and in order that the present contribution to the art may be better appreciated. There are of course additional features of the invention that will be described below and which will form the subject matter of the invention.

In this respect, before explaining at least one embodiment of the invention in detail, it is to be understood that the invention is not limited in its application to the arrangements of the components set forth in the following description or illustrated in the drawings. The invention is capable of other embodiments and can be practised and carried out in various ways. Also it is to be understood that the phraseology and terminology employed herein as well as the abstract, are for the purpose of the description and should not be regarded as limiting.

As such, those skilled in the art will appreciate that the conception upon which this disclosure is based may readily be utilised as a basis for the designing of other structures, and methods for carrying out several purposes of the present invention. It is important therefore that the claims are to be regarded as including such equivalent constructions insofar as they do not depart from the spirit and scope of the present invention.

BRIEF DESCRIPTION OF THE DRAWINGS

The present invention will be further described by way of example with reference to the accompanying drawings, in which.

DESCRIPTION OF PREFERRED EMBODIMENT

Figure 1:
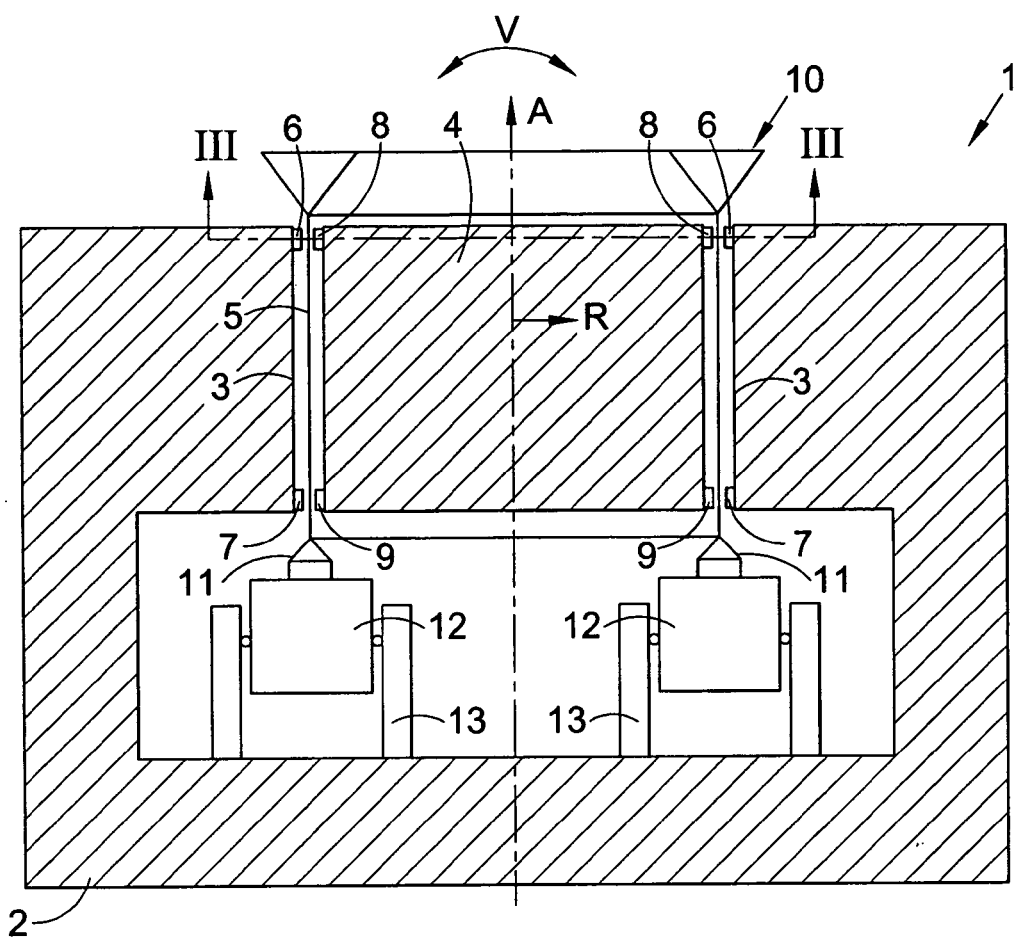
FIG. 1 is a sketch cross section through a vibration testing apparatus according to the present invention.

FIG. 1 is a sketch cross sectional view through the vibration testing apparatus according to the present invention, generally designated 1.

The vibration testing apparatus 1 comprises a rigid support 2, formed of a rigid, massive material, for example cast metal such as cast steel. The support 2 includes an annular face 3 facing an annular space, in which is mounted an annular body 5 which will be described further below.

The support further comprises an inner body 4 in the form of a cylindrical section, which is supported by structures which are not shown and which is provided to support the annular body 5 on the inside.

The annular body 5 is mounted to the support on its outer surface at the top by bearings 6 and at the bottom by bearings 7. It is mounted to the inner body 4 at its inner surface by bearings 8 at the top and bearings 9 at the bottom.

At the top, the annular body 5 is connected to an annular head expander 10.

Together, the annular body 5 and the head expander 10 form a mounting for an annular piece of equipment to be tested (not shown). They may each be made of light magnesium alloy, for a combination of strength and lightness.

Figure 6:
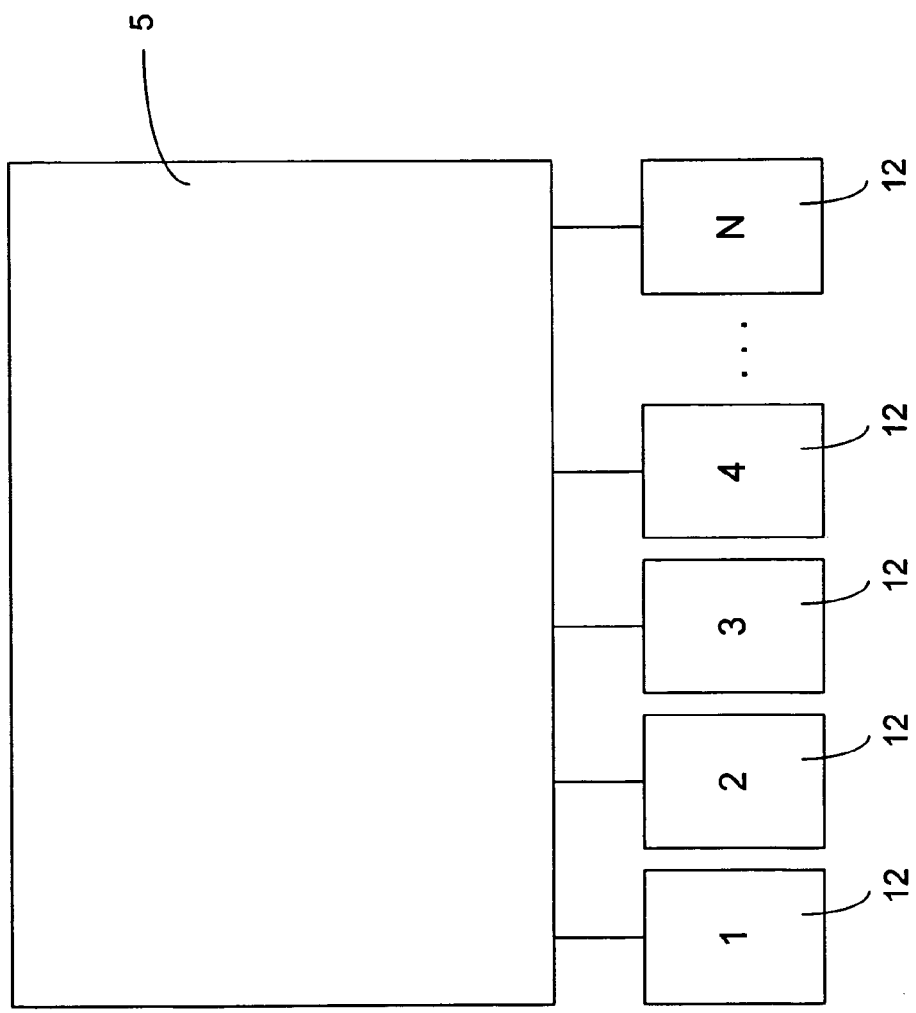
FIG. 6 is a schematic diagram of the annular body of a mounting used in the vibration testing apparatus of FIG. 1, with one through N electromagnetic vibration generators illustrated.

The annular body 5 is connected at the bottom to armatures 11 of electromagnetic vibration generators 12. As shown in FIG. 6, any number of electromagnetic vibration generators 12 may be used. For example, two are shown in FIG. 1, but three or four may be used instead.

The electromagnetic vibration generators are each mounted on support structures 13 which are themselves rigidly mounted in the support 2.

Any suitable design of vibration generator 12 may be used, for example as described in GB2217521.

Each of the bearings 6, 7, 8 and 9 comprise hydrostatic bearings. Sources of pressurised bearing fluid (not shown) will be provided in a manner known in the art.

In FIG. 1, the arrow R denotes the radial direction. Arrow A denotes the axial direction. The curved arrow V denotes a rocking direction of rigid vibrational modes of equipment to be tested mounted on the head expander 10. It is desired in the invention to reduce the amplitude and/or increase the frequency of vibrational modes in the direction V whilst allowing the apparatus to be relatively flexible in the radial direction R so that vibrational forces can be transmitted from the generators 12 to the equipment to be tested.

Figure 2:
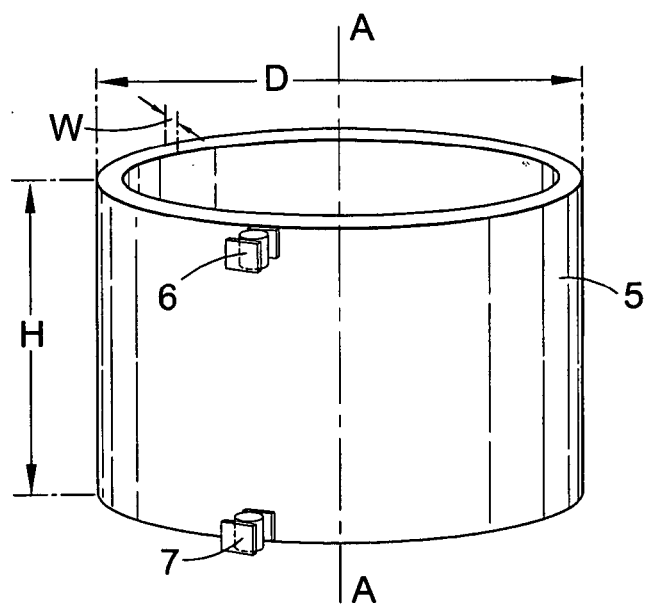
FIG. 2 is a sketch isometric view of the annular body of a mounting used in the vibration testing apparatus of FIG. 1, with one set of bearings illustrated.

FIG. 2 is a sketch isometric view of the annular body 5 of FIG. 1. It can be seen that it comprises an annular body 5 of diameter D which is in the range 1–3.0 meters and a height H, in the axial direction A, of about 3.0 meters. The radial extent or width W of the annular body will be selected to give adequate stiffness so that there are substantially no flexing vibration modes in the frequency range of interest (5–150 Hz). In this case, the radial width W is of the order of 0.1 meters.

One set of bearings 6, 7 is shown schematically on the outer face of the annular member 5. In practice, as will be clear in FIG. 3, many more sets of bearings will be provided.

Figure 3:
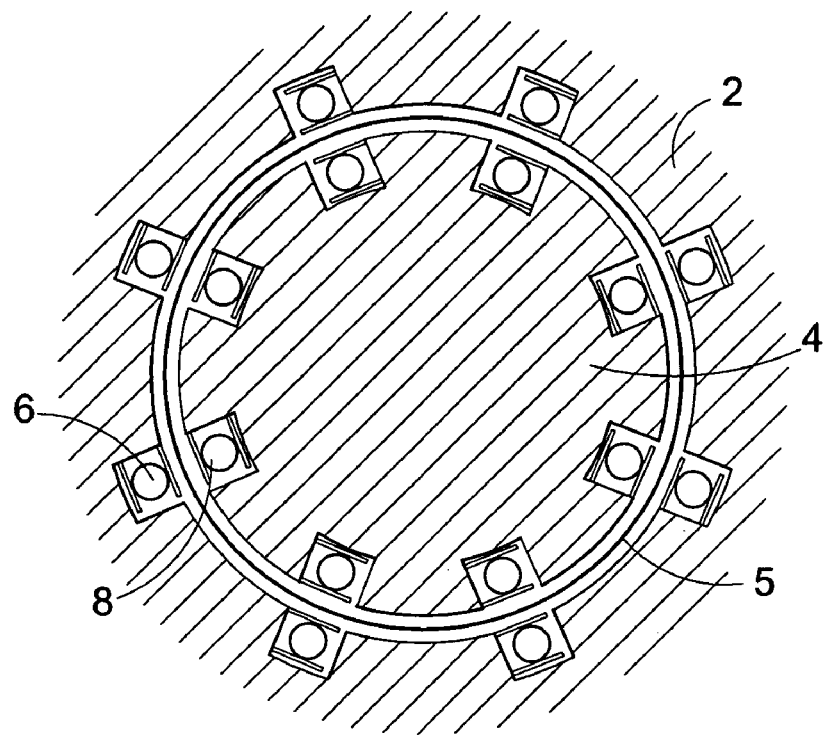
FIG. 3 is a partial sketch cross sectional view along line III—III of FIG. 1.

In FIG. 3, eight sets of bearings are schematically shown, but in practice many more may be used if necessary. They are placed at regular angular intervals around the periphery of the annular member 5. A sufficient number of bearings will be provided in order to give good stiffness.

Figure 4:
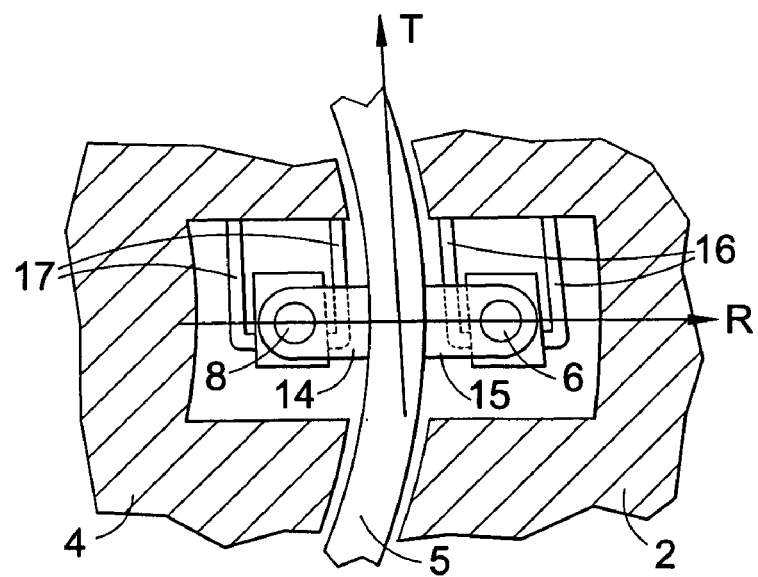
FIG. 4 is a partial illustration, at enlarged scale, of one of the bearings shown in FIG. 3.

FIG. 4 is a part cross sectional view of one of the bearing sets. Each of the bearing sets comprises hydrostatic bearings 6 and 8 of known design. Each is mounted to the annular body 5 by a short, rigid arm 14 or 15 respectively. These arms 14 and 15 have substantially no vibrational modes in the frequency range of interest.

However, the bearings 6 and 8 are each mounted to the respective part of the support 2, 4 by a bearing arm 16, 17 respectively. The bearing arms 16 and 17 are designed so that they are rigid in the tangential direction T but are relatively flexible in the radial direction R. Further, the bearing 6 and 8 are designed so that annular body 5 is substantially unconstrained in the axial direction A so that vibrational forces can be transmitted from the electromagnetic vibration generators 12 through the annular body 5 and the head expander 10 to equipment to be tested.

Figure 5:
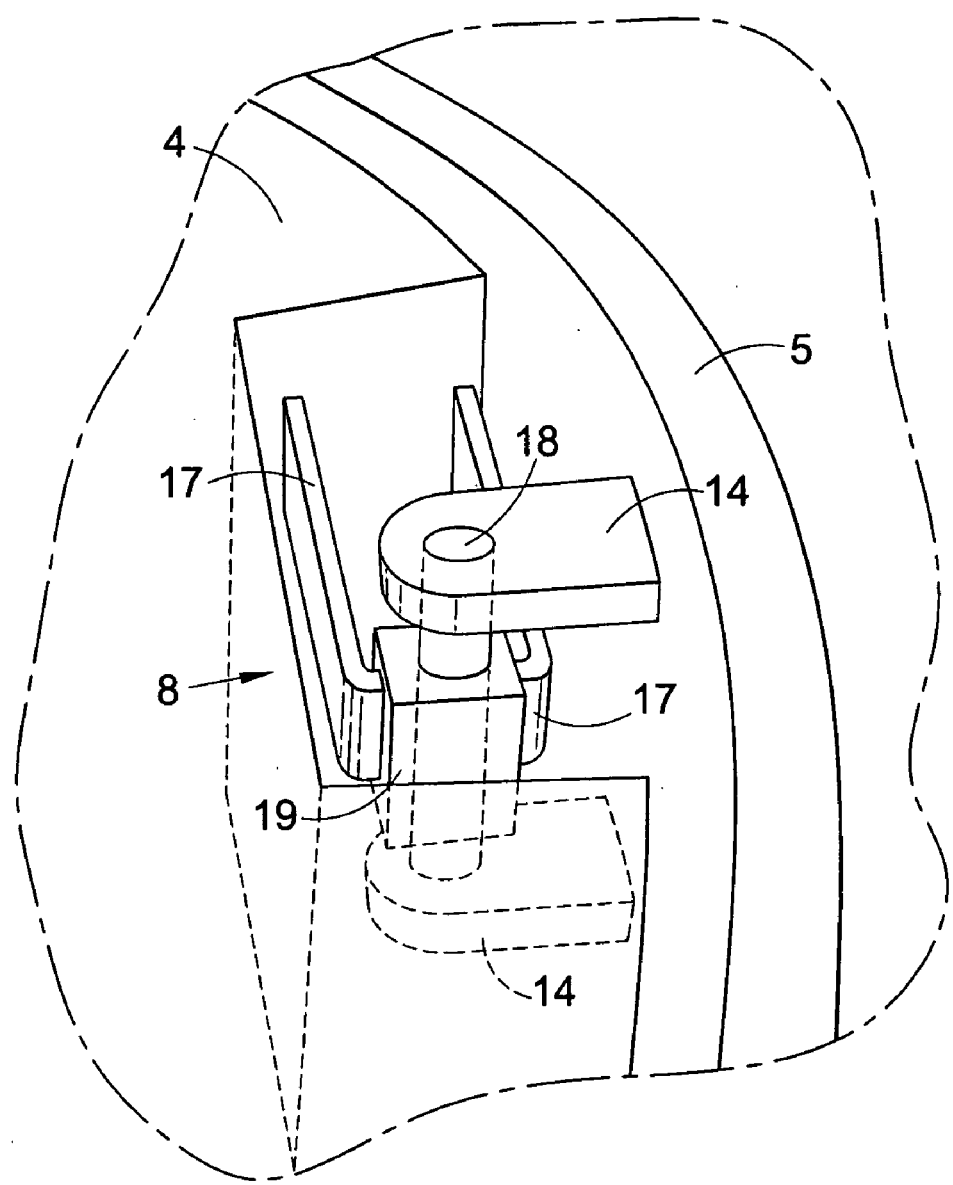
FIG. 5 is sketch partial isometric view, at enlarged scale, of part of the bearing shown in FIG. 4.

FIG. 5 is a partial sketch isometric view of the bearing shown in FIG. 4. Only the bearing 8 is shown. The bearing 6 is not shown, for clarity. It can be seen that the bearing comprises a pair of rigid arms 14 and a pair of rigid arms 17 as described in relation to FIG. 4. A shaft 18, which extends in the axial direction A extends between the arms 14 and is received in a bearing receiver 19 which is mounted on the other pair of arms 17. The shaft 18 is axially slidable within the bearing receiver 19, so that the annular body 5 is axially unconstrained by the bearing 8, within the limits imposed by the arms 14. The whole weight of the mounting and the equipment to be tested is then taken by the vibration generators 12. This design of bearing also allows the effect of thermal expansion to be accommodated.

The clearances permitted by hydrostatic bearings 6, 8 are very small. This can give problems due to thermal expansion or due to differential loading of the annular ring 5 by equipment to be tested. However, the flexible support for the bearings 6, 8 allows such variations to be taken up without causing the bearings to jam.

The many features and advantages of the invention are apparent from the detailed description of the embodiment above, and thus it is intended by the appended claims to cover all such features and advantages of the invention which fall within the spirit and the scope of the invention. Further, since numerous modifications and variations will readily occur to those skilled in the art, it is not desired to limit the invention to the exact construction and operation illustrated and described and accordingly, all suitable modifications and equivalents may be resorted to, falling within the scope of the invention.

What is claimed is:

1. A vibration testing apparatus, comprising:
   a support;
   at least one electromagnetic vibration generator mounted on the support;
   a mounting drivable by the at least one electromagnetic vibration generator;
   wherein the mounting comprises an annular body supported on the support by at least one hydrostatic bearing including at least one bearing arm extending generally in a tangential direction of the annular body.

2. The vibration testing apparatus according to claim 1, wherein the outer diameter of the annular body is at least 1.0 m.

3. The vibration testing apparatus according to claim 1, wherein the outer diameter of the annular body is at least 2.0 m.

4. A vibration testing apparatus according to claim 1, wherein the radial extent of the annular body is in the range less than 0.5 m.

5. A vibration testing apparatus according to claim 1, wherein the radial extent of the annular body is in the range less than 0.2 m.

6. A vibration testing apparatus according to claim 1, wherein the radial extent of the annular body is in the range less than 0.1 m.

7. A vibration testing apparatus according to claim 1, wherein the mounting comprises an annular body and a head expander.

8. A vibration testing apparatus according to claim 1, wherein the annular body has a height which is preferably greater than or equal to at least 0.5 times the diameter of the annular body.

9. A vibration testing apparatus according to claim 1, wherein the annular body has a height which is preferably greater than or equal to at least 0.7 times the diameter of the annular body.

10. A vibration testing apparatus according to claim 1, wherein the annular body has a height which is preferably greater than or equal to at least 1 times the diameter of the annular body.

11. The vibration testing apparatus according to claim 1, wherein bearings are mounted at the top and bottom of the annular body.

12. The vibration testing apparatus according to claim 1, wherein bearings are mounted on the inside and the outside of the annular body.

13. A vibration testing apparatus according to claim 1, comprising at least two electromagnetic vibration generators.

14. A vibration testing apparatus according to claim 1, comprising at least three electromagnetic vibration generators.

15. A vibration testing apparatus according to claim 1, comprising at least four electromagnetic vibration generators.

16. A vibration testing apparatus according to claim 1, wherein the at least one bearing comprises a bearing shaft having a bearing axis which is aligned with the axis of the annular body, the bearing shaft being received in a bearing receiver so that the bearing shaft is displaceable along its axis within the bearing receiver, so that the annular body is substantially unconstrained in its axial direction.

17. A vibration testing apparatus according to claim 1, wherein the mounting is composed of magnesium alloy.

18. A method of vibration testing, comprising mounting equipment to be tested on a mounting, the mounting being drivable in vibrational modes by at least one electromagnetic vibration generator, the electromagnetic vibration generator being mounted on a support, the mounting comprising an annular body supported on the support by at least one hydrostatic bearing including at least one bearing arm extending generally in a tangential direction of the annular body.

19. A method of vibration testing according to claim 18, wherein the equipment to be tested is fixed to the mounting.

20. A method of vibration testing according to claim 19, wherein the mounting further comprises a head expander and the equipment to be tested is fixed to the head expander.

21. A method of vibration testing according to claim 18, wherein the electromagnetic vibration generator is used to generate vibrations having frequencies in the range 5–150 Hz.

22. A method of vibration testing according to claim 18, wherein the mounting is vibrated along its axis, the bearing being relatively flexible in the radial direction and relatively stiff in the tangential direction.

23. A vibration testing apparatus, comprising:

a support;

at least one electromagnetic vibration generator mounted on the support;

a mounting drivable by the at least one electromagnetic vibration generator;

wherein the mounting comprises an annular body supported on the support by at least one bearing including a bearing shaft having a bearing axis which is aligned with the axis of the annular body, the bearing shaft being received in a bearing receiver so that the bearing shaft is displaceable along its axis within the bearing receiver, so that the annular body is substantially unconstrained in its axial direction.

24. A vibration testing apparatus according to claim 23, wherein the bearings comprise hydrostatic bearings.

25. A vibration testing apparatus according to claim 24, wherein the hydrostatic bearings comprise bearing arms extending generally in a tangential direction of the annular body.

* * * * *